(12) United States Patent
Ceppi et al.

(10) Patent No.: US 11,103,005 B2
(45) Date of Patent: Aug. 31, 2021

(54) HOLDER FOR AEROSOL GENERATING ARTICLE

(71) Applicant: PHILIP MORRIS PRODUCTS S.A., Neuchatel (CH)

(72) Inventors: François Ceppi, Sugiez (CH); Ali Murat Saygili, Neuchatel (CH)

(73) Assignee: Philip Morris Products S.A., Neuchâtel (CH)

( * ) Notice: Subject to any disclaimer, the term of this patent is extended or adjusted under 35 U.S.C. 154(b) by 3 days.

(21) Appl. No.: 16/066,458

(22) PCT Filed: Dec. 6, 2016

(86) PCT No.: PCT/IB2016/057394
§ 371 (c)(1),
(2) Date: Jun. 27, 2018

(87) PCT Pub. No.: WO2017/115185
PCT Pub. Date: Jul. 6, 2017

(65) Prior Publication Data
US 2019/0150505 A1 May 23, 2019

(30) Foreign Application Priority Data
Dec. 29, 2015 (EP) .................................... 15202961

(51) Int. Cl.
*A24F 13/14* (2006.01)
*A24F 13/02* (2006.01)
(Continued)

(52) U.S. Cl.
CPC ................ *A24F 13/14* (2013.01); *A24D 1/22* (2020.01); *A24F 13/02* (2013.01); *A24F 42/10* (2020.01); *A61M 15/06* (2013.01); *A24F 42/60* (2020.01)

(58) Field of Classification Search
CPC ........... A24F 13/14; A24F 13/16; A24F 13/02
See application file for complete search history.

(56) References Cited

U.S. PATENT DOCUMENTS 1,347,204 A * 7/1920 Bridges ................... A24F 13/08
131/188
1,447,664 A * 3/1923 Hollingsworth ........ A24F 13/08
131/182
(Continued)

FOREIGN PATENT DOCUMENTS

JP        S5191186 U     7/1976
JP        S52-143170 A   11/1977
(Continued)

OTHER PUBLICATIONS

International Search Report and Written Opinion issued by the European Patent Office as the International Searching Authority, for PCT/IB2016/057394, dated Mar. 29, 2017; 14 pgs.
(Continued)

*Primary Examiner* — Eric Yaary
*Assistant Examiner* — Jennifer A Kessie
(74) *Attorney, Agent, or Firm* — Mueting Raasch Group

(57) ABSTRACT

A holder (200) for an aerosol generating article (100) includes a body (210) defining a passage configured to receive the article. The holder also includes a retainer (240) longitudinally moveable relative to the body from a first position to a second position. The retainer comprises a deflectable arm (242) and a retention member (247) extending from the arm and configured to retain the article within the passage of the body when the retainer is in the first position. Movement of the retainer to the second position causes the arm to deflect to provide access for introducing or withdrawing the article from the passage of the body. The holder may include a plurality of retainers moveable from a first position to the second position. The plurality of retain-
(Continued)

ers may surround a combustible heat source (102) of the aerosol generating article when the retainers are in the first position.

20 Claims, 6 Drawing Sheets

(51) Int. Cl.
*A24D 1/22* (2020.01)
*A24F 42/10* (2020.01)
*A61M 15/06* (2006.01)
*A24F 42/60* (2020.01)

(56) References Cited

U.S. PATENT DOCUMENTS

| | | |
|---|---|---|
| 1,527,519 A | 2/1925 | Kimball |
| 2,314,585 A | 3/1943 | Lemle |
| 2,454,631 A | 11/1948 | Chneerson et al. |
| 2,768,630 A | 10/1956 | Johnson |
| 3,796,223 A * | 3/1974 | Tarrant .................... A24F 13/10 131/182 |
| 5,040,552 A | 8/1991 | Schleich et al. |
| 5,595,577 A | 1/1997 | Bensalem et al. |
| 2010/0258139 A1 * | 10/2010 | Onishi .................. A24F 47/006 131/194 |
| 2015/0027458 A1 | 1/2015 | Grant et al. |

FOREIGN PATENT DOCUMENTS

| | | |
|---|---|---|
| JP | 59-154092 U | 10/1984 |
| JP | 2015-509706 | 4/2015 |
| WO | WO 98/54989 A1 | 12/1998 |
| WO | WO 2009/022232 A2 | 2/2009 |
| WO | WO 2013/076098 A2 | 5/2013 |

OTHER PUBLICATIONS

Japanese Office Action for JP2018-533927, issued by the Japanese Patent Office dated Jan. 28, 2021; 7 pgs. including English translation.

* cited by examiner

HOLDER FOR AEROSOL GENERATING ARTICLE

This application is the § 371 U.S. National Stage of International Application No. PCT/IB2016/057394, filed 6 Dec. 2016, which claims the benefit of European Application No. 15202961.7, filed 29 Dec. 2015.

This invention relates to an aerosol generating article having a combustible heat source for heating an aerosol generating substrate and a holder for the article.

A number of aerosol generating articles in which tobacco is heated rather than combusted have been proposed in the art. An aim of such 'heated' smoking articles is to reduce certain smoke constituents of the type produced by the combustion and pyrolytic degradation of tobacco in conventional cigarettes.

In one known type of aerosol generating article, an aerosol is generated by the transfer of heat from a combustible heat source to a physically separate aerosol generating substrate, for example containing tobacco. The aerosol generating substrate may be located within, around or downstream of the combustible heat source. During use, volatile compounds are released from the aerosol generating substrate by heat transfer from the combustible heat source and entrained in air drawn through the smoking article. As the released compounds cool, they condense to form an aerosol that is inhaled by the user.

Heated smoking articles and aerosol generating articles in general may be configured so that the combustible heat source is blind, which may limit the amount or number volatile compounds released from combustion of the heat source that enter air drawn through the smoking article. Heated smoking articles having blind combustible heat sources may transfer heat to the aerosol generating substrate primarily via conduction. Heated smoking articles may also be configured so that the heat source is non-blind. Heated smoking articles having non-blind combustible heat sources transfer heat to the aerosol generating substrate primarily via convection through one or more air flow channels through the heat source, which allow volatile compounds from the heat source to enter air drawn through the smoking article. Because one aim of heated smoking articles is to reduce certain smoke constituents produced via combustion, heated smoking articles employing blind heat sources may be preferred.

Published PCT patent application, WO-A2-2009/022232, discloses an example of a heated smoking article having a non-blind heat source. The heated smoking article disclosed in WO-A2-2009/022232 comprises a combustible heat source, an aerosol generating substrate downstream of the combustible heat source, and a heat conducting element around and in contact with a rear portion of the combustible heat source and an adjacent front portion of the aerosol generating substrate. An air flow channel extends through the heat source such that air may be drawn through the channel downstream towards a mouthpiece.

Regardless of whether heated smoking articles include a blind or non-blind combustible heat source, the heat source may require direct contact with air to burn properly. Thus, heated smoking articles may be manufactured such that the heat source is exposed to a smoker and their surroundings during smoking. However, temperatures of the combustible heat sources may be quite high when burning. For example, temperatures of the heat sources during combustion may be more than 600° C.

One advantage of at least some examples of the invention is to reduce the temperature of an exposed element to which a user of an aerosol generating article having a combustible heat source or their environment may be exposed. Another advantage of at least some examples of the invention is to facilitate extinguishment of a combustible heat source of an aerosol generating article. Another advantage of at least some examples of the invention is to maintain a blind heat source while reducing the temperature of an exposed element to which a user or their environment may be exposed.

In various aspects, the invention provides holder for an aerosol generating article. The holder comprises a body defining a passage configured to receive the aerosol generating article. The holder also comprises a retainer longitudinally moveable relative to the body from a first position to a second position. The retainer comprises a deflectable arm and a retention member extending from the arm and configured to retain the aerosol generating article within the passage of the body when the retainer is in the first position. Movement of the retainer to the second position causes the arm to deflect to provide access for introducing or withdrawing the aerosol generating article from the passage of the body.

The holder may comprise a plurality of retainers moveable from a first position to the second position. The plurality of retainers may surround a combustible heat source of the aerosol generating article when the retainers are in the first position. The retainers that surround the combustible heat source may be spaced apart. Preferably, the retainers allow for sufficient air flow for continued combustion of the surrounded heat source. Preferably, the heat source can be ignited by, for example, a flame while surrounded by the retainers. The holder may comprise a sleeve slidable over the retainers. The sleeve restricts airflow through the retainers to the heat source to extinguish the heat source.

A holder according to the invention may be configured to prevent or reduce the number or amount volatile compounds released from the heat source during combustion from entering air drawn through the aerosol generating article and inhaled by a user. For example, a holder may include a seal extending from an inner surface of, for example, the body. The seal may be arranged to surround and engage the aerosol generating article between the heat source and, for example, the aerosol generating substrate to limit volatile compounds released from the heat source during combustion from entering drawn through the aerosol generating article. The body may include through holes downstream of the seal to allow air flow into the aerosol generating article. Where air inlets are present in the aerosol generating article, the through holes of the body may be arranged to allow air external to the body to be drawn through the holes, through the air inlets of the aerosol generating article and into a mouth of a user. The through holes may enhance air flow over the aerosol generating substrate to increase release of volatile compounds from the substrate, to increase delivery of volatile compounds to a user, or increase release of volatile compounds from the substrate and increase delivery of volatile compounds to a user.

The term "aerosol generating article" refers to an article comprising an aerosol generating substrate that releases volatile compounds to form an aerosol that may be inhaled by a user. The term "aerosol generating substrate" refers to a substrate capable of releasing, upon heating, volatile compounds, which may form an aerosol. The aerosols generated from aerosol generating substrates of articles according to the invention may be visible or invisible and may include vapours (for example, fine particles of substances, which are in a gaseous state, that are ordinarily liquid or solid at room temperature) as well as gases and liquid droplets of condensed vapours.

The terms "distal," "upstream," "proximal," and "downstream" are used to describe the relative positions of components, or portions of components, of an aerosol generating article. Aerosol generating articles according to the invention have a proximal end through which, in use, an aerosol exits the article for delivery to a user, and have an opposing distal end. The proximal end of the aerosol generating article may also be referred to as the mouth end. In use, a user draws on the proximal end of the aerosol generating article in order to inhale an aerosol generated by the aerosol generating article. The terms upstream and downstream are relative to the direction of aerosol movement through the aerosol generating article when a user draws on the proximal end.

Various aspects of the aerosol generating articles and holders according to the present invention may have one or more advantages relative to currently available aerosol generating articles that include a combustible heat source. For example, holders according to the invention provide a simple to use barrier to protect a smoker or their surrounding environment from contact with a combusted heat source having a high temperature. When the retainers are in the first position and surround the heat source, the retainers may be separated from the heat source so that the temperature of the retainers is lower than the temperature of the combusted heat source. The retainers may be configured to efficiently dissipate heat to reduce temperature of the retainers relative to the combusted heat source. By way of further example, a holder of the invention can facilitate extinguishment by an easy to use, simple mechanical mechanism. Simply sliding the sleeve over the retainers while the heat source is surrounded by the retainers may result in extinguishment of the heat source. In some preferred embodiments, holders according to the invention are configured to prevent or reduce the number or amount volatile compounds released from the heat source during combustion from entering air drawn through the aerosol generating article and inhaled by a user. For example, a holder may include a seal extending from an inner surface of the body. The seal may be arranged to surround and seal the aerosol generating article between the heat source and, for example, the aerosol generating substrate to limit volatile compounds released from the heat source during combustion from entering drawn through the aerosol generating article. Additional advantages of one or more aspects of aerosol generating articles described herein will be evident to those of skill in the art upon reading and understanding the present disclosure.

The present invention relates to an aerosol generating article having a combustible heat source for heating an aerosol generating substrate and a holder for the aerosol generating article. The holder includes one or more retainers configured to retain the aerosol generating article in the holder. Preferably, the holder comprises more than one retainer. The retainers may be configured to surround a heat source of the aerosol generating article. The retainers may be separated from the heat source so that the temperature of the retainers is lower than the temperature of the combusted heat source. The retainers can also be configured to efficiently dissipate heat to reduce temperature of the retainers relative to the combusted heat source. In use, the temperature of the retainers is substantially lower than the heat source during combustion. Accordingly, the temperature of an element to which a user of the aerosol generating article may be exposed is reduced. The holder may also comprise a sleeve slidable over the retainers for extinguishing the heat source when a user has finished using the aerosol generating article.

A holder according to the present invention comprises a body having a proximal end and a distal end. The body defines a passage from the proximal end to the distal end for receiving an aerosol generating article. Preferably, the passage is configured to receive an aerosol generating article having a combustible heat source. The body may be configured to slidably receive the aerosol generating article into the passage through the distal end. In addition or alternatively, the body may define a window or recess for lateral insertion of the aerosol generating article. The passage defines an inner surface of the body. Preferably, at least a portion of the inner surface of the body engages the aerosol generating article when the article is received in the passage. For example, the inner surface of the body may define one or more detents or one or more reduced inner diameter portions that are configured to engage the aerosol generating article by interference fit. In addition or alternatively, the passage may be sized to engage the aerosol generating article along its length.

Alternatively, one or more additional elements disposed in the passage may engage the aerosol generating article. Regardless of whether the inner surface of the body is configured to engage the aerosol generating article or whether an additional element in the passage is configured to engage the aerosol generating article, the aerosol generating article is preferably retained in a longitudinal position relative to the body in use. The aerosol generating article is preferably insertable or removable from the passage with minimal force. For example, the aerosol generating article may be readily inserted or withdrawn from the passage by a user.

In preferred embodiments, the body defines one or more through holes. The through holes are arranged and configured to be downstream of a heat source the aerosol generating article that the body is configured to receive. The through holes allow air to be drawn through the body, into an aerosol generating article received by the body, and into a user's mouth. Where air inlets are present in the aerosol generating article, the through holes of the body may be arranged to allow air external to the body to be drawn through the holes and through the air inlets of the aerosol generating article. The through holes may enhance air flow over the aerosol generating substrate to increase release of volatile compounds from the substrate, to increase delivery of volatile compounds to a user, or increase release of volatile compounds from the substrate and increase delivery of volatile compounds to a user. The holes through the body, if present, may be downstream of a seal, if present.

Preferably, a holder comprises a seal to prevent or reduce the number or amount combustion products released from the heat source from entering air drawn through the aerosol generating article and inhaled by a user. For purposes of the present disclosure, a "seal" includes a baffle or other element that blocks or substantially inhibits volatile combustion compounds from a heat source from passing through the element when the element is incorporated into a holder of the invention.

A seal may extend from an inner surface of the body and may be arranged to surround and engage the aerosol generating article between the heat source and, for example, the aerosol generating substrate.

The seal may have any suitable inner diameter. Preferably, the inner diameter of the seal, in a relaxed state, is less than the outer diameter of the aerosol generating article. The seal may deflect to allow insertion of the aerosol generating article through the seal. The seal may aid in holding the body in a longitudinal position relative to the aerosol generating article.

The seal may be integrally formed with the body or attached to the body in any suitable manner. The seal may be formed of any suitable material or combination of materials. Because the seal is configured to be placed in proximity to the heat source, the seal preferably comprises heat resistant materials. The seal preferably comprises a resilient material. Examples of materials that may be used to form a seal or a portion thereof include plastic materials and elastomers, for example nitrile or fluorocarbons (viton) materials.

A body according to the invention may be formed of any suitable material or combination of materials. For example, the body may be formed from a material comprising a polymer, such as a thermoplastic polymer, or a material comprising a metal, such as aluminium. In addition or alternatively, the body may be formed from material comprising wood, carbon fibre or glass fibre. Preferably, the body comprises a semi-crystalline polymer. Examples of suitable polymers from which the body or a portion of the body may be made include polyehther ether ketone (PEEK), polyoxymethylene (POM), high density polyethylene (HDPE) and the like.

A holder according to the invention comprises one or more retainers. The retainers are longitudinally moveable over the body from a first position to a second position. Each retainer comprises a deflectable arm and a retention member extending from the arm. The retainer is configured to retain the aerosol generating article within the passage of the body when the retainers are in the first position. When the retainers are moved to the second position, the arms deflect to provide access for introducing or withdrawing the aerosol generating article from the passage of the body.

Preferably, a deflectable arm of a retainer includes a bend portion. The bend portion may extend beyond the body when the retainer is in the first position. The bend portion may contact an exterior surface of the body when the retainer is in the second position, which causes the arm to deflect. The bend portion may be positioned between proximal and distal portions. The proximal and distal portions may extend substantially in a planar manner when in a relaxed state. When arranged in the holder and the retainer is in the first position, the bend portion may project towards the longitudinal axis of the body. Preferably, the bend portion projects towards the longitudinal axis of body to a distance less than the outer diameter of the body. As the retainer is moved from the first, extended position to the second, refracted position, the bend portion interacts with body to cause the distal port of the arm to deflect. A distal end of the body may be rounded or tapered to facilitate movement of the arm, particularly, the bend portion, over the distal end of the body as the retainer is moved from the first position to the second position.

The retainers, when in the first, extended position, are preferably arranged and configured to surround a heat source of the aerosol generating article received in the passage of the body. When surrounding the heat source, the retainers may be space apart and may form a cage about the heat source. The cage may define an inner diameter greater than the outer diameter of the heat source of the aerosol generating article. As used herein, the term 'diameter' denotes the maximum dimension in the transverse direction of the combustible heat source, aerosol generating article, holder, cage or other apparatus or component. As used herein, the terms 'radial' and 'transverse' are used to describe the direction perpendicular to the longitudinal direction. The distance between the retainers and the heat source, the material of the retainers, the thickness of the retainers, and the permeability of the cage formed by the retainers, among other factors, may be selected to control the maximum temperature, relative to the heat source when in use.

Preferably, the retainers reach a maximum temperature substantially lower than the heat source when the heat source is combusted and is disposed within the cylindrical cage formed by the retainers. For example, a temperature at an exposed surface of the retainers may be at least 200° C. less than the temperature of a surface of the heat source. Preferably, a temperature at an exposed surface of the retainers may be at least 300° C. less than the temperature of a surface of the heat source. For example, when the heat source temperature is about 400° C., preferably the exposed surface of the retainer is less than about 200° C., preferably less than about 150° C.

The retainers may be separated from the heat source by any suitable distance when the retainers are in the first position. For example, the radial clearance between the heat source and the retainers may be between about 0.2 mm and about 3 mm. Preferably, the axial clearance between the heat source and the body of the retainers is between about 0.5 mm and about 1 mm. For example, the radial clearance between the retainers and the heat source may be about 0.5 mm or less.

A cage defined by the retainers about the heat source has sufficient permeability to allow air to access the heat source around the retainers to maintain combustion of the heat source. The term "permeability" refers to a percent of total area of a surface or a portion of a surface that is void space area. Space between the retainers forming the cage around the heat source may provide for permeability. For example, the retainers may occupy less than 50% of the circumferential area around the heat source. Preferably at least a portion of the cage formed by the retainers has sufficient permeability to allow a lighting of the heat source by, for example, a flame.

The retainers may have any suitable length. Preferably, the retainers have a length of about 10 mm or less. For example, the retainers may have a length of about 6 mm or less. Generally, the length of the retainers will be greater than 1 mm.

The retainers may be formed of any suitable material or materials. Preferably, the retainers comprise a heat resistant material. For example, the retainers or portions of the retainers may be formed from a heat resistant polymeric material or a heat resistant metallic material. Preferably, the retainers comprise a metallic material. For example, the retainers may comprise aluminum or stainless steel. In one preferred embodiment, the retainers are formed from stamped stainless steel.

Preferably, the retainers or the arms of the retainers are formed from material having a high elasticity limit so that the arms are within the elastic deformation zone of the material when the arms are bent.

Preferably, the retainers are coupled to an actuator slidable over the body. Sliding of the actuator may cause the retainers to move between the first, extended position and the second, retraced position. The actuator may have any suitable form. For example, the actuator may be a ring disposed about the body or a sleeve disposed about the body. Preferably, the actuator is a sleeve disposable about the body.

In some preferred embodiments, a distal portion of the sleeve extends over at least a portion of the bend portions of the retainers. Preferably, the radial clearance between an inner surface of the sleeve and the bend portions of the retainers is sufficient to allow deflection of the arms when the retainers are in the second, retracted position. In addition or alternatively, the distal portion of the sleeve is sufficiently flexible to allow the arms to deflect. A seal may extend from an inner surface of the distal portion of the sleeve and may be arranged to surround and engage the aerosol generating article between the heat source and, for example, the aerosol-generating substrate. In some preferred embodiments, the seal extends into the bends of the arms of the retainers into spaces between bends of adjacent retainer arms. The seal may be integrally formed with the sleeve or attached to the sleeve in any suitable manner. The seal may be a seal as described above regarding the seal interacting with the body.

If a seal extends from a distal portion of the sleeve, the sleeve preferably includes air inlets downstream of the seal. The air inlets are arranged and configured to be downstream of a heat source. The air inlets allow air to be drawn through the sleeve, into an aerosol generating article received by the body, and into a user's mouth. Where air inlets are present in the aerosol generating article, the air inlets of the sleeve may be arranged to allow air external to the sleeve to be drawn through the holes and through the air inlets of the aerosol generating article.

Preferably, the actuator, whether the actuator is a sleeve, ring, or other element, interacts with the body such that the actuator may be retained in a distal position in which the retainers are in the first, extended position and a proximal position in which the retainers are in the second, retracted position. For example, the actuator may comprise a longitudinal opening, for example a slit, through which a post of, or attached to, the body can extend. The proximal and distal ends of the longitudinal opening may, along with the post, define the distal and proximal positions of the actuator.

A holder according to the invention may also comprise an extinguishment sleeve configured to extinguish the heat source of the smoking article. The extinguishment sleeve may be slidably disposed over the body between a retracted position and an extended position. In the extended position, the extinguishment sleeve is configured to surround at least a portion of the heat source and restrict air flow to heat source. The extinguishment sleeve may be formed of any suitable material or materials and be of any suitable structure to have a sufficiently low permeability to extinguish the heat source. In some preferred embodiments, the extinguishment region of the sleeve comprises a polymeric or metallic solid walled portion. However, the extinguishment region may include air inlets, for example perforations, or may otherwise allow air flow, provided that the air flow is not sufficient to maintain combustion of the heat source. In some preferred embodiments, the extinguishment sleeve is configured to slide over the retainers when the retainers are in the first extended position and surrounding the heat source.

The extinguishment region may be separated from the heat source by any suitable distance. For example, the radial clearance between the heat source and the extinguishment region may be between about 0.5 mm and about 3 mm. Preferably, the radial clearance between the heat source and the extinguishment region is between about 1 mm and about 2 mm. For example, the radial clearance between the extinguishment region and the heat source may be about 0.5 mm or less.

The sleeve may be formed from one or more suitable materials. Preferably, the sleeve comprises a polymeric material. More preferably, the sleeve comprises a semi-crystalline polymeric material. Examples of suitable polymeric materials of which the sleeve or portions of the sleeve can be made include polyether ether ketone (PEEK), polyoxymethylene (POM) and high density polyethylene (HDPE). The sleeve may comprise metallic materials. For example, the sleeve may comprise aluminium or stainless steel.

Preferably, the extinguishment sleeve interacts with the body such that the actuator may be retained in the extended or retracted position. For example, the extinguishment sleeve may comprise a longitudinal opening, for example a slit, through which a post of, or attached to, the body can extend. The proximal and distal ends of the longitudinal opening may, along with the post, define the distal and proximal positions of the actuator. In some preferred embodiments, the extinguishment sleeve is slidable over the retainer actuator.

Preferably, the extinguishment sleeve is also retainable in an intermediate position between the extended or retracted position. In the intermediate position, a distal end of the sleeve extends over at least a portion of the bend portions of the retainers. A seal may extend from an inner surface of the extinguishment sleeve and may be arranged to surround and engage the aerosol generating article between the heat source and, for example, the aerosol-generating substrate. In some preferred embodiments, the seal extends into the bends of the arms of the retainers into spaces between bends of adjacent retainer arms. The seal may be integrally formed with the extinguishment sleeve or attached to the sleeve in any suitable manner. The seal may be a seal as described above regarding the seal interacting with the body.

The extinguishment sleeve may be moved to the retracted position prior or simultaneously with movement of the retainers to the second, retracted position to allow deflection of the arms of the retainers.

If a seal extends from the extinguishment sleeve, the sleeve preferably includes air inlets downstream of the seal. The air inlets are arranged and configured to be downstream of a heat source. The air inlets allow air to be drawn through the sleeve, into an aerosol generating article received by the body, and into a users mouth. Where air inlets are present in the aerosol generating article, the air inlets of the sleeve may be arranged to allow air external to the sleeve to be drawn through the holes and through the air inlets of the aerosol generating article.

A holder according to the present invention may include a mouthpiece. The body may extend to form the mouthpiece or the mouthpiece may be connected to the body. The mouthpiece has a mouth end and a distal end. The mouthpiece defines a passage between the mouth end and the distal end for flow of aerosol from the aerosol generating article.

The mouthpiece may be telescoping and may adapt a collapsed, ejection position and an expanded, use position. Preferably, the mouth end is movable distally relative to the distal end to the collapsed position to eject the aerosol generating article from the holder. The mouth end may be biased, for example via a spring, towards the expanded position so the mouth end moves distally relative to the distal end after a pushing force, for example to collapse the mouthpiece, is removed. A tube may be disposed in the mouthpiece and extend into the passage of the body. As the mouth end of the telescoping mouthpiece is pressed and moved distally, the tube may press against the aerosol generating article and cause the article to move distally.

A holder according to the present invention may be configured to allow an aerosol generating article to be inserted into a passage the body when the retainers are in the second, retracted position in which the arms are deflected to provide access for introducing or withdrawing the aerosol generating article from the passage. Once the aerosol generating article is inserted into the passage of the body, an actuator coupled to the retainers may be advanced over the body until the retainers are in the first, expanded position in which the retainers form a cage about a heat source of the aerosol generating element. While the retainers are in the first, expanded position and surrounding the heat source, the heat source may be ignited by, for example, a flame. If the extinguishment sleeve includes a seal, the extinguishment sleeve may be moved to the intermediate position to position the seal downstream of the heat source to prevent or limit combustion products from the heat source from entering air drawn through the aerosol generating article from entering a user's mouth. Alternatively and optionally, a seal may extend from an actuator sleeve or the body as described above. A user may draw on the mouth end of the aerosol generating article or the mouthpiece of the holder, if present, to inhale aerosol from the aerosol generating article. When the user has completed a use of the article, the extinguishment sleeve may be advanced over the retainers to extinguish the heat source. Once the heat source is extinguished, the retainers may be moved to the second retracted position such that the arms of the retainers deflect to provide access for the withdrawal or ejection of the aerosol generating article from the passage. If the holder comprises a telescoping mouthpiece, the mouth end of the mouth piece may be pressed and moved distally relative to the body to eject the aerosol generating article from the holder once the heat source has been extinguished.

Holders according to the present invention may be used with any suitable aerosol generating article having a combustible heat source. The aerosol generating article includes an aerosol generating substrate that may be heated by the combustible heat source to release one or more volatile compounds from the aerosol generating substrate.

An aerosol generating article for use with a holder according to the present invention may include any suitable combustible heat source.

The combustible heat source is preferably a blind combustible heat source. As used herein, the term 'blind' describes a heat source that does not comprise any air flow channels that provide inhalation air to the aerosol generating substrate. In a blind combustible heat source, heat transfer from the blind combustible heat source to the aerosol generating substrate occurs primarily by conduction and heating of the aerosol generating substrate by forced convection is minimized or reduced. The lack of any airflow channels through the blind combustible heat source advantageously substantially prevents or inhibits activation of combustion of the blind combustible heat source during puffing by a user. This substantially prevents or inhibits spikes in the temperature of the aerosol generating substrate during puffing by a user. By preventing or inhibiting activation of combustion of the blind combustible heat source, and so preventing or inhibiting excess temperature increases in the aerosol generating substrate, combustion or pyrolysis of the aerosol generating substrate under intense puffing regimes may be advantageously avoided. In addition, the impact of a user's puffing regime on the composition of the mainstream aerosol may be advantageously minimized or reduced. The inclusion of a blind combustible heat source may also advantageously substantially prevent or inhibit combustion and decomposition products and other materials formed during ignition and combustion of the blind combustible heat source from entering air drawn through the aerosol generating article during use thereof.

Alternatively, the combustible heat source comprises at least one longitudinal airflow channel, which provides one or more inhalation airflow pathways through the heat source to the aerosol generating substrate. This inhalation airflow channel may extend along the length of the heat source through which air may be drawn through the aerosol generating article for inhalation by a user. Such heat sources including one or more longitudinal inhalation airflow channels are referred to herein as "non-blind" heat sources.

The combustible heat source is preferably a carbonaceous heat source having a carbon content of at least about 35 percent, more preferably of at least about 40 percent, most preferably of at least about 45 percent by dry weight of the combustible heat source. Where the combustible heat source is a carbonaceous heat source, the combustible heat source may be formed from one or more suitable carbon-containing materials. The term "carbonaceous" refers to a material that comprises carbon.

The combustible heat source may be a combustible carbon-based heat source having a carbon content of at least about 50 percent. For example, the combustible heat source may be a combustible carbon-based heat source having a carbon content of at least about 60 percent, or at least about 70 percent, or at least about 80 percent by dry weight of the combustible heat source. The term "carbon-based" refers to a material comprises primarily of carbon or at least about 50% carbon, by dry weight of material.

One or more binders may be combined with the one or more carbon-containing materials to form the carbonaceous heat source. The combustible heat source may comprise one or more organic binders, one or more inorganic binders or a combination of one or more organic binders and one or more inorganic binders.

Instead of, or in addition to one or more binders, the combustible heat source may comprise one or more additives in order to improve the properties of the combustible heat source. Suitable additives include, but are not limited to, additives to promote consolidation of the combustible heat source (for example, sintering aids), additives to promote ignition of the combustible heat source (for example, oxidisers such as perchlorates, chlorates, nitrates, peroxides, permanganates, zirconium and combinations thereof), additives to promote combustion of the combustible heat source (for example, potassium and potassium salts, such as potassium citrate) and additives to promote decomposition of one or more gases produced by combustion of the combustible heat source (for example catalysts, such as CuO, $Fe_2O_3$ and $Al_2O_3$). Combustible heat sources for aerosol generating articles and methods for producing such heat sources are known in the art and described in, for example, U.S. Pat. Nos. 5,040,552 and 5,595,577.

Preferably, the combustible heat source has an apparent density of between about 0.8 $g/cm^3$ and about 1.1 $g/cm^3$. Preferably, the combustible heat source has a mass of between about 300 mg and about 500 mg, more preferably of between about 400 mg and about 450 mg. Preferably, the combustible heat source has a length of between about 7 mm and about 17 mm, more preferably of between about 7 mm and about 15 mm, most preferably of between about 7 mm and about 13 mm. Preferably, combustible heat sources according to the invention have a diameter of between about 5 mm and about 9 mm, more preferably of between about 7 mm and about 8 mm.

Preferably, the combustible heat source is of substantially uniform diameter. However, the combustible heat source may alternatively be tapered such that the diameter of one of the front end face and the rear end face of the combustible heat source is greater than the diameter of the other of the front end face and the rear end face thereof. For example, combustible heat sources may be tapered such that the diameter of the rear end face of the combustible heat source is greater that the diameter of the front end face of the combustible heat source. Preferably, the combustible heat source is substantially cylindrical. The combustible heat source may be a cylindrical combustible heat source of substantially circular cross-section or of substantially elliptical cross-section. In particularly preferred embodiments, the combustible heat source is a substantially cylindrical combustible heat source of substantially circular cross-section.

An aerosol generating article for use with a holder according to the invention may include any aerosol generating substrate.

Preferably, the aerosol generating substrate comprises at least one aerosol-former and a material capable of releasing volatile compounds in response to heating. The aerosol generating substrate may comprise other additives and ingredients including, but not limited to, humectants, flavorants, binders and mixtures thereof. Preferably, the aerosol generating substrate comprises nicotine. More preferably, the aerosol generating substrate comprises tobacco.

The at least one aerosol-former may be any suitable known compound or mixture of compounds that, in use, facilitates formation of a dense and stable aerosol and that is substantially resistant to thermal degradation at the operating temperature of the aerosol generating article. Suitable aerosol-formers are well known in the art and include, for example, polyhydric alcohols, esters of polyhydric alcohols, such as glycerol mono-, di- or triacetate, and aliphatic esters of mono-, di- or polycarboxylic acids, such as dimethyl dodecanedioate and dimethyl tetradecanedioate. Preferred aerosol formers for use in aerosol generating articles herein are polyhydric alcohols or mixtures thereof, such as triethylene glycol, 1,3-butanediol and, most preferred, glycerin.

The material capable of emitting volatile compounds in response to heating may be a charge of plant-based material. The material capable of emitting volatile compounds in response to heating may be a charge of homogenized plant-based material. For example, the aerosol generating substrate may comprise one or more materials derived from plants including, but not limited to: tobacco; tea, for example green tea; peppermint; laurel; eucalyptus; basil; sage; verbena; and tarragon. Preferably, the material capable of emitting volatile compounds in response to heating is a charge of tobacco-based material, most preferably a charge of homogenized tobacco based material.

The aerosol generating substrate may be in the form of a plug or segment comprising a material capable of emitting volatile compounds in response to heating circumscribed by a paper or other wrapper. As stated above, where an aerosol generating substrate is in the form of such a plug or segment, the entire plug or segment including any wrapper is considered to be the aerosol generating substrate. The aerosol generating substrate preferably has a length of between about 5 mm and about 20 mm. Preferably, the aerosol generating substrate has a length of between about 6 mm and about 15 mm or a length of between about 7 mm and about 12 mm. In preferred embodiments, the aerosol generating substrate comprises a plug of tobacco-based material wrapped in a plug wrap. In particularly preferred embodiments, the aerosol generating substrate comprises a plug of homogenised tobacco-based material wrapped in a plug wrap.

Holders according to the present invention may be used with any suitable aerosol generating article.

Aerosol generating articles for use with holders according to the present invention may comprise one or more air inlets around the periphery of the aerosol generating substrate. In such embodiments, in use, cool air is drawn into the aerosol generating substrate of the aerosol generating article through the air inlets. The air drawn into the aerosol generating substrate through the air inlets passes downstream through the aerosol generating article from the aerosol generating substrate and exits the aerosol generating article through the mouthpiece or proximal end thereof.

In such embodiments, during puffing by a user the cool air drawn through the one or more air inlets around the periphery of the aerosol generating substrate advantageously reduces the temperature of the aerosol generating substrate. This advantageously substantially prevents or inhibits spikes in the temperature of the aerosol generating substrate during puffing by a user. As used herein, the term 'cool air' is used to describe ambient air that is not significantly heated by the combustible heat source upon puffing by a user.

Aerosol generating articles described herein may comprise a heat conducting element around and in direct contact with both at least a rear portion of the heat source and at least a front portion of the aerosol generating substrate. The heat conducting element provides a thermal link between the combustible heat source and the aerosol generating substrate and advantageously helps to facilitate adequate heat transfer from the combustible heat source to the aerosol generating substrate to provide an acceptable aerosol.

Suitable heat conducting elements for use herein include, but are not limited to: metal foil wrappers such as, for example, aluminum foil wrappers, steel wrappers, iron foil wrappers and copper foil wrappers; and metal alloy foil wrappers.

Aerosol generating articles described herein may comprise a mouthpiece located at the proximal end thereof. Preferably, the mouthpiece is of low filtration efficiency, more preferably of very low filtration efficiency. The mouthpiece may be a single segment or component mouthpiece. Alternatively, the mouthpiece may be a multi-segment or multi-component mouthpiece.

The mouthpiece may comprise a filter comprising one or more segments comprising suitable known filtration materials. Suitable filtration materials are known in the art and include, but are not limited to, cellulose acetate and paper. Alternatively or in addition, the mouthpiece may comprise one or more segments comprising absorbents, adsorbents, flavorants, and other aerosol modifiers and additives or combinations thereof.

Aerosol generating articles described herein preferably further comprise a transfer element or spacer element between the aerosol generating substrate and the mouthpiece. The transfer element may abut one or both of the aerosol generating substrate and the mouthpiece. Alternatively, the transfer element may be spaced apart from one or both of the aerosol generating substrate and the mouthpiece.

The inclusion of a transfer element advantageously allows cooling of the aerosol generated by heat transfer from the combustible heat source to the aerosol generating substrate. The inclusion of a transfer element also advantageously allows the overall length of the aerosol generating article to be adjusted to a desired value, for example to a length similar to that of a conventional cigarette, through an appropriate choice of the length of the transfer element.

The transfer element may have a length of between about 7 mm and about 50 mm, for example a length of between about 10 mm and about 45 mm or of between about 15 mm and about 30 mm. The transfer element may have other lengths depending upon the desired overall length of the aerosol generating article, and the presence and length of other components within the aerosol generating article.

Preferably, the transfer element comprises at least one open-ended tubular hollow body. In such embodiments, in use, air drawn into the aerosol generating article passes through the at least one open-ended tubular hollow body as it passes downstream through the aerosol generating article from the aerosol generating substrate to the mouthpiece. The transfer element may comprise at least one open-ended tubular hollow body formed from one or more suitable materials that are substantially thermally stable at the temperature of the aerosol generated by the transfer of heat from the combustible heat source to the aerosol generating substrate. Suitable materials are known in the art and include, but are not limited to, paper, cardboard, plastics, such a cellulose acetate, ceramics and combinations thereof.

Alternatively or in addition, aerosol generating articles described herein may comprise an aerosol cooling element or heat exchanger between the aerosol generating substrate and the mouthpiece. The aerosol cooling element may comprise a plurality of longitudinally extending channels. The aerosol cooling element may comprise a gathered sheet of material selected from the group consisting of metallic foil, polymeric material, and substantially non-porous paper or cardboard. In certain embodiments, the aerosol-cooling element may comprise a gathered sheet of material selected from the group consisting of polyethylene (PE), polypropylene (PP), polyvinylchloride (PVC), polyethylene terephthalate (PET), polylactic acid (PLA), cellulose acetate (CA), and aluminum foil. Preferably the aerosol-cooling element may comprise a gathered sheet of biodegradable polymeric material, such as polylactic acid (PLA) or a grade of Mater-Bi® (a commercially available family of starch based copolyesters).

The aerosol generating articles described herein may comprise an outer wrapper that circumscribes the aerosol generating substrate and at least a rear portion of the heat source or heat source holder. The outer wrapper should grip the heat source and heat source holder and the aerosol generating substrate of the aerosol generating article when the aerosol generating article is assembled. Preferably the outer wrapper circumscribes the aerosol generating substrate, at least a rear portion of the heat source and heat source holder and any other components of the aerosol generating article downstream of the aerosol generating substrate. Outer wrappers may be formed from any suitable material or combination of materials. Suitable materials are well known in the art and include, but are not limited to, cigarette paper. Alternatively or in addition, the mouthpiece may be circumscribed by tipping paper. Aerosol generating articles described herein may be assembled using known methods and machinery.

The aerosol generating article may be substantially cylindrical in shape. The aerosol generating or may be substantially elongate. The aerosol generating or has a length and a circumference substantially perpendicular to the length. The aerosol generating substrate may be substantially cylindrical in shape. The aerosol generating substrate may be substantially elongate. The aerosol generating substrate also has a length and a circumference substantially perpendicular to the length. The aerosol generating substrate may be located in the aerosol generating or such that the length of the aerosol generating substrate is substantially parallel to the airflow direction in the aerosol generating article. The transfer section or element may be substantially elongate.

The aerosol generating article may have any desired length. For example, the aerosol generating article may have a total length of between approximately 65 mm and approximately 100 mm. The aerosol generating article may have any desired external diameter. For example, the aerosol generating article may have an external diameter of between approximately 5 mm and approximately 12 mm.

One or more of the filter, transfer element, aerosol cooling element, and heat exchanger may be incorporated into a holder of the present invention rather than being included in the aerosol generating article. The length of the aerosol generating article may be reduced if one or more of the filter, transfer element, aerosol cooling element, and heat exchanger are incorporated into the holder. In some preferred embodiments, the holder comprises one or more of the filter, transfer element, aerosol cooling element, and heat exchanger, and the holder is re-usable.

All scientific and technical terms used herein have meanings commonly used in the art unless otherwise specified. The definitions provided herein are to facilitate understanding of certain terms used frequently herein.

As used herein, the singular forms "a", "an", and "the" encompass embodiments having plural referents, unless the content clearly dictates otherwise.

As used herein, "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising," and the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

Reference will now be made to the drawings, which depict one or more aspects described in this disclosure. However, it will be understood that other aspects not depicted in the drawing fall within the scope and spirit of this disclosure. Like numbers used in the figures refer to like components, steps and the like. However, it will be understood that the use of a number to refer to a component in a given figure is not intended to limit the component in another figure labeled with the same number. In addition, the use of different numbers to refer to components in different figures is not intended to indicate that the different numbered components cannot be the same or similar to other numbered components.

The schematic drawings are not necessarily to scale and are presented for purposes of illustration and not limitation.

Figure 1:
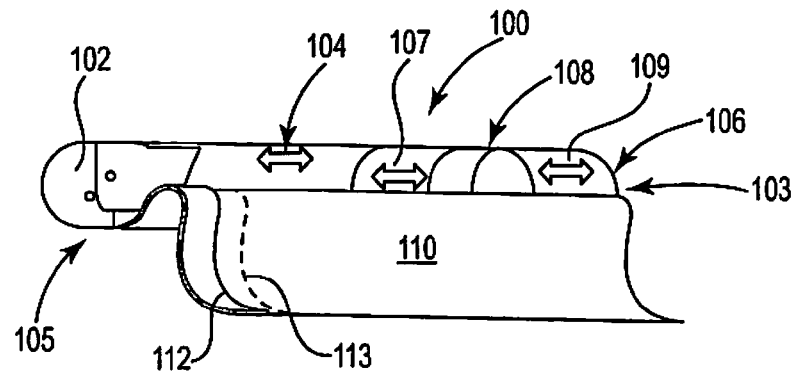
FIG. 1 is schematic perspective view of an illustrative aerosol generating article with the wrapper partially opened to view the internal contents.

Referring now to FIG. 1, an aerosol generating article 100 extends between a proximal end 103 and a distal end 105. The aerosol generating article 100 includes a combustible heat source 102 positioned at the distal end 105 of the aerosol generating article 100, an aerosol generating substrate 104 downstream of the combustible heat source 102 and a mouthpiece 106 downstream of the aerosol generating substrate 104 and positioned at the proximal end 103 of the aerosol generating article 100.

The aerosol generating article 100 comprises a combustible heat source 102, an aerosol generating substrate 104, an aerosol cooling element 107, an elongate expansion chamber or transfer element 108 and a mouthpiece 106, are in sequential, abutting coaxial alignment, which are overwrapped in an outer wrapper 110 of, for example, cigarette paper. The combustible heat source 102 is cylindrical.

The aerosol generating substrate 104 is located immediately downstream of the combustible heat source 102 and comprises a cylindrical plug of homogenized tobacco material comprising, for example, glycerin as aerosol former and circumscribed by filter plug wrap. A heat conducting element 112, consisting of a tube of aluminum foil, surrounds and is in contact with a rear portion of the combustible heat source 102 and an abutting front portion of the aerosol generating substrate 104. The elongate expansion chamber 108 is located downstream of the aerosol generating substrate 104 and comprises a cylindrical open-ended tube of cardboard. The mouthpiece 106 is located downstream of the expansion chamber 108 and comprises a cylindrical plug of cellulose acetate tow 109 circumscribed by filter plug wrap.

In use, the user ignites the combustible heat source which heats the aerosol generating substrate to produce an aerosol. When the user inhales on the mouthpiece 106 air is drawn through the aerosol generating substrate 104 through air inlet holes 113 in the cigarette paper 110 and adjacent to the aerosol generating substrate 104, through the expansion chamber 108, through the mouthpiece 106 and into the user's mouth.

Figure 2:
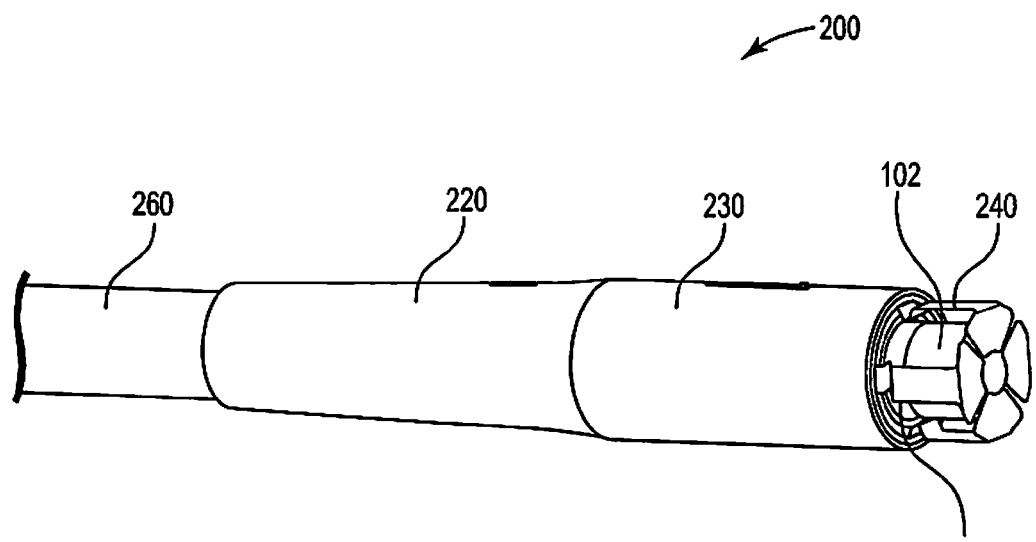
FIGS. 2 and 3 are schematic perspective views of a portion of an illustrative holder in which an illustrative aerosol generating article is inserted.
Figure 3:
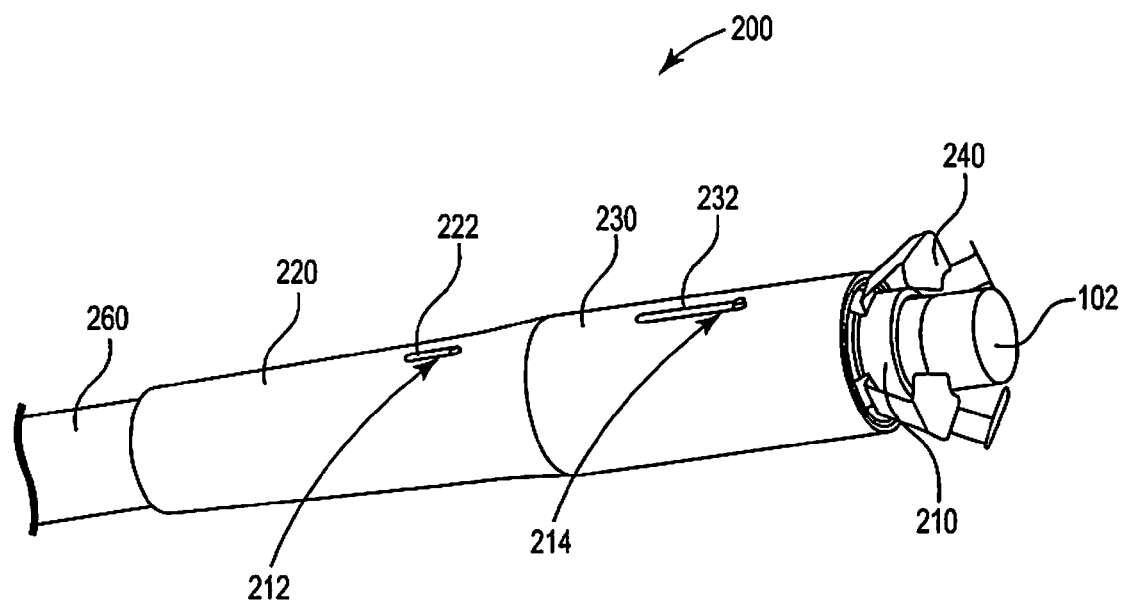

Referring now to FIGS. 2 and 3, schematic perspective views of an aerosol generating article having a combustible heat source 102 disposed in a holder 200 are shown. The illustrated holders 200 include a body 210, mouthpiece 260, first sleeve 220, second sleeve 230, and retainers 240. The retainers 240 are coupled to the first sleeve 220. Distal advancement of the first sleeve 220 over the body 210 causes the retainers 240 to adapt an extended first configuration in which the retainers 240 surround the heat source 102 (FIG. 2). Space between adjacent retainers 240 allow for sufficient air flow to the heat source 102 to ignite the heat source 102, for example with a flame, and to allow for continued combustion of the heat source. The retainers 240 are separated from the heat source so that the temperature of the retainers is lower than the temperature of the combusted heat source. The retainers 240 may also efficiently dissipate heat to reduce temperature of the retainers relative to the combusted heat source. Accordingly, the retainers 240 provide a barrier to protect a smoker or their surrounding environment from contact with a combusted heat source having a high temperature.

When the first sleeve 220 is withdrawn proximally over the body 210, bend portions of the retainers 240 engage the body 210, causing arms of the retainers 240 to outwardly deflect (FIG. 3) to provide access to allow the aerosol generating article having the heat source 102 to be introduced into the holder 200 or withdrawn or ejected from the holder 200.

Figure 4:
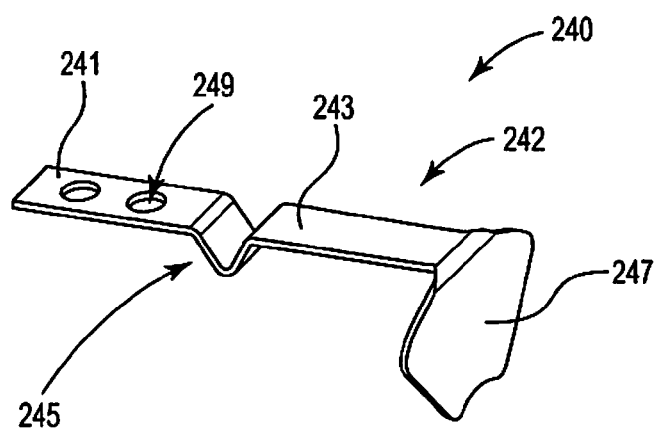
FIG. 4 is a schematic perspective view of an illustrative retainer.

Referring now to FIG. 4, a retainer 230 includes a deflectable arm 242 and a retention member 247 extending from the arm 242. The deflectable arm 242 includes a bend portion 245 between a proximal arm portion 241 and a distal arm portion 243. When the retainer 240 is included in a holder, the bend portion 243 may extend beyond the body of the holder when the retainer is in the first position. The bend portion 243 may contact an exterior surface of the body when the retainer is in the second position, which causes the arm to deflect. The proximal 241 and distal 243 portions of the arm 242 extend substantially in a planar manner when in a relaxed state (depicted in FIG. 4). When arranged in the holder and the retainer 240 is in the first position, the bend portion 243 may project towards the longitudinal axis of the body of the holder. Preferably, the bend portion 243 projects towards the longitudinal axis of body to a distance less than the outer diameter of the body. As the retainer 243 is moved from the first, extended position to the second, retracted position, the bend portion 243 interacts with body to cause the distal portion 243 of the arm 242 to deflect.

When included in a holder, the retention member 247 extends from the distal arm portion 243 towards a longitudinal axis of the holder. The retention member 247 extends towards the longitudinal axis of the holder greater than the ben portion 234.

As shown in FIG. 4, the retainer 240 may include fastening elements, for example through holes 249, for securing to the retainer 240 to an actuator, for example a first sleeve, in any suitable manner, for example rivets through the through holes 249.

Referring now to FIGS. 5A, 5B, 6A, 6B, 7A, 7B, 8A and 8B, a holder 200 includes a body 210, a first sleeve 220, a second sleeve 230, retainers 240, a tube 250, a mouthpiece 260 and a spring 270. The body 210 defines a passage for receiving an aerosol generating article 100 having a heat source 102. A proximal portion of the body 210 has a reduced inner diameter configured to engage the aerosol generating article 100 via interference fit and may define a shoulder against which the proximal end of the aerosol generating article 100 interacts to prevent further proximal insertion of the article 100 into body 210.

Figure 5A:
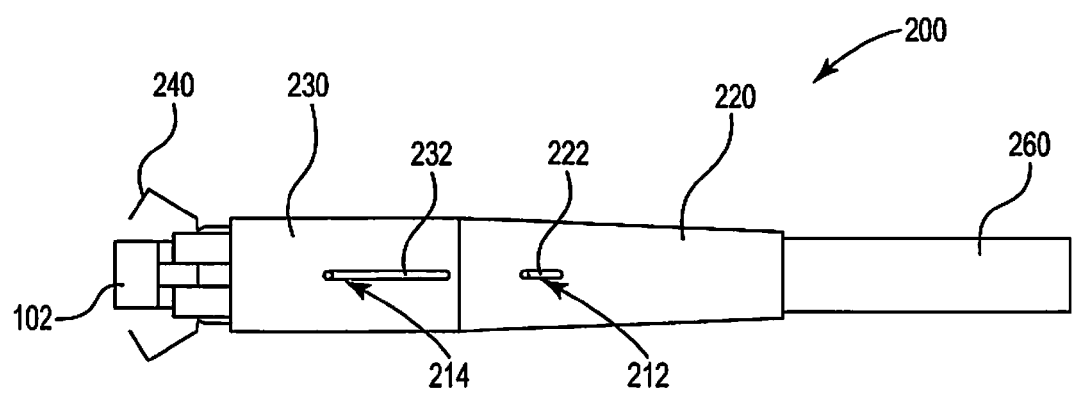
FIGS. 5A, 6A, 7A and 8A are schematic side views of an illustrative aerosol generating article in an illustrative holder.
Figure 8A:
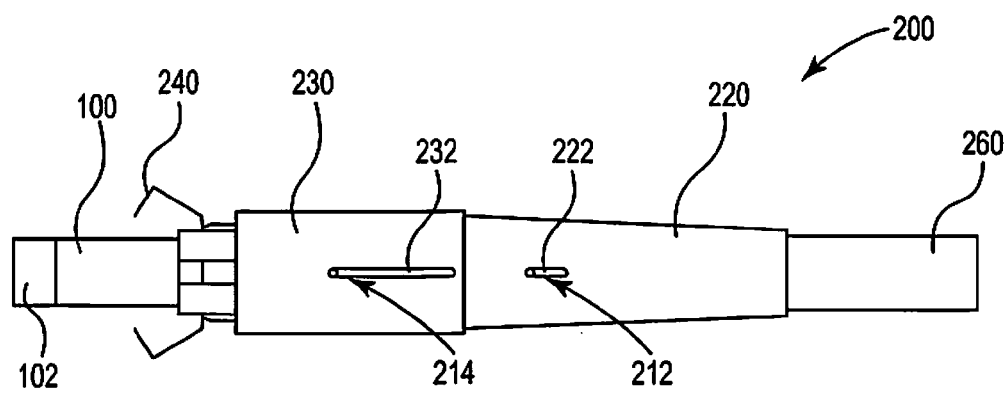

The retainers 240 are coupled to the first sleeve 220 such that moving, for example sliding, the sleeve 220 over the body 210 causes the retainers 240 to move longitudinally relative to the body 210 between a first, extended position (FIG. 6A) and a second, retracted position (FIG. 5A, FIG. 8A). In the first, extended position the retainers 240 form a cage that surrounds the heat source 102. In the second, retracted position, bend portions of the arms of the retainers 240 interact with the body 210 to deflect the arms.

The first sleeve 220 defines a longitudinal opening 222 through which post 212 extends. Post 212 is coupled to or is an extension of the body 210. The distance that the sleeve 220 can move longitudinally relative to the body 210 is defined by the length of opening 222 and the diameter of post 212. When the post 212 abuts the distal end of the opening 222, the first sleeve 220 is in a retracted position. When the post 212 abuts the proximal end of the opening 222, the first sleeve 220 is in an extended position.

Figure 6A:
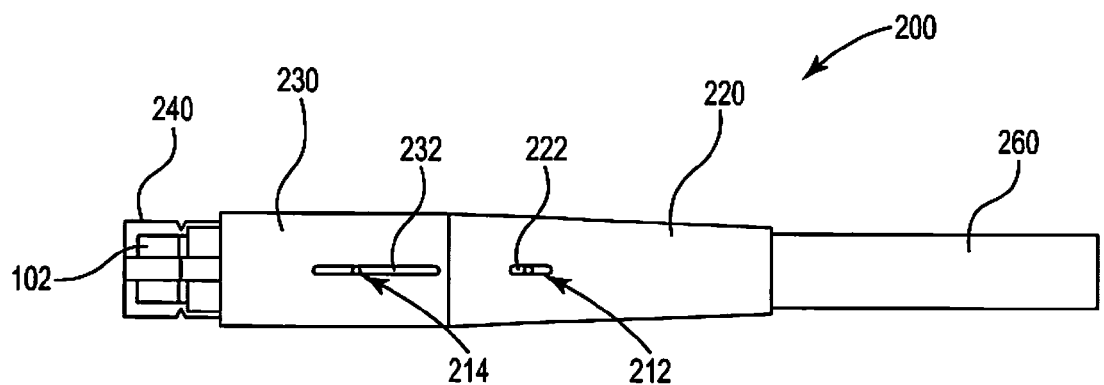
Figure 7A:
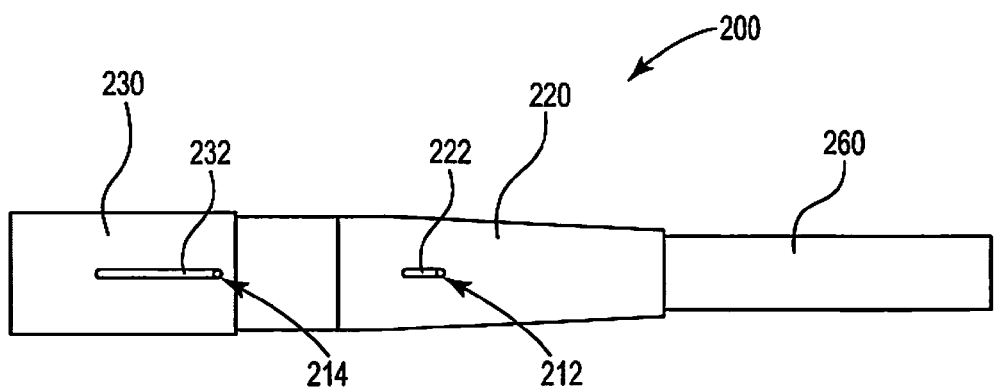

The second sleeve 230 is an extinguishment sleeve that slides over the first sleeve 220 between a retracted position (FIG. 5A, FIG. 6A, FIG. 8A) to an extended extinguishment position (FIG. 7A). In the extended position, a distal portion of the second sleeve 230 is disposed over the retainers 240 and serves to restrict air flow to the heat source 102 in through the space between adjacent retainers 240.

The second sleeve 230 defines a longitudinal opening 232 through which post 214 extends. Post 214 is coupled to or is an extension of the body 210. The distance that the sleeve 230 can move longitudinally relative to the body 210 is defined by the length of opening 232 and the diameter of post 214. When the post 214 abuts the distal end of the opening 232, the second sleeve 230 is in a retracted position. When the post 214 abuts the proximal end of the opening 232, the second sleeve 220 is in an extended, extinguishment position.

The mouthpiece 260 couples to the body 210 or may be an extension of the body 210. The mouthpiece 260 is telescoping. Tube 250 is disposed in mouthpiece 260 and body 210. Spring 270 interacts with body 210 and mouthpiece 260 to bias mouthpiece 260 to a use position.

Figure 5B:
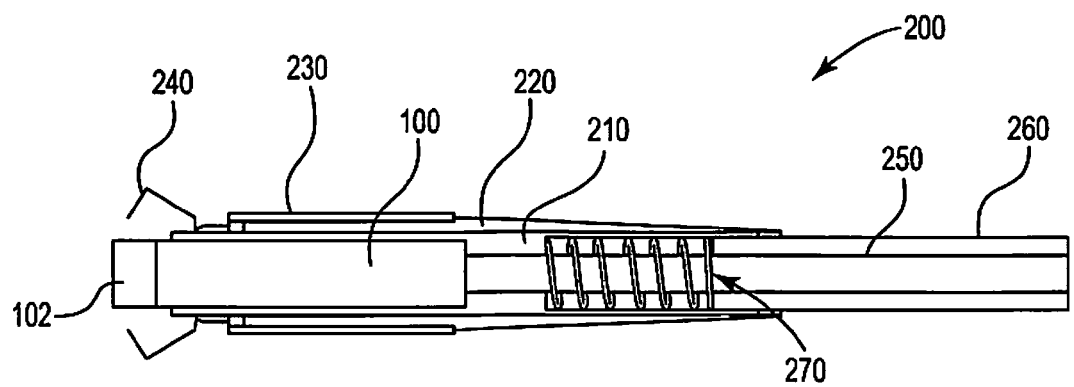
FIGS. 5B, 6B, 7B and 8B are schematic views of the aerosol generating article and holder illustrated in FIGS. 5A, 6A, 7A and 8A, respectively, with a portion of the holder cut-away.

In FIGS. 5A and 5B the holder 200 is in an insertion position in which an aerosol generating article 100 having a heat source 102 may be inserted into a passage of the body 210 of the holder 200. The retainers 240 are deflected retracted to allow insertion of aerosol generating article 100. The heat source may be ignited when the holder is in the insertion position or may be ignited when the heat source 102 is in the use position.

Figure 6B:
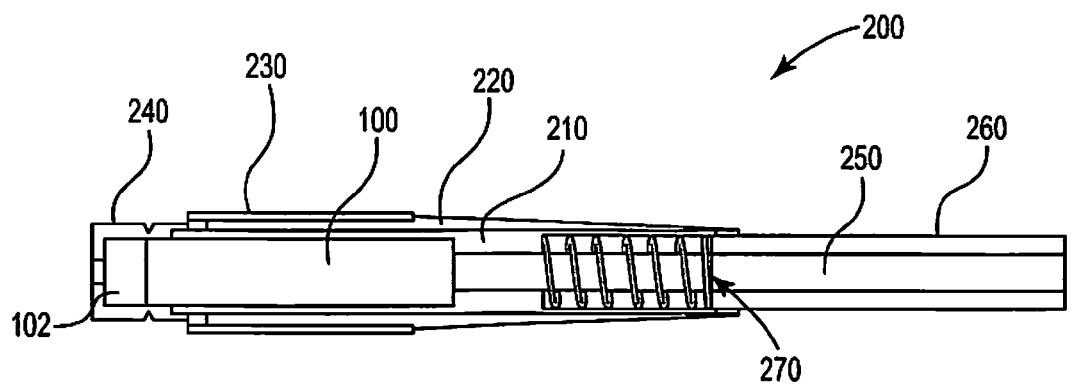

In FIGS. 6A and 6B the holder 200 is in a use position in which the heat source 102 of the aerosol generating article 100 is surrounded by retainers 240. The configuration and arrangement of the retainers 240 surrounds the heat source 102 and provides sufficient air flow to the heat source 102 to allow the heat source 102 to be ignited and to maintain combustion of the heat source 102.

Figure 7B:
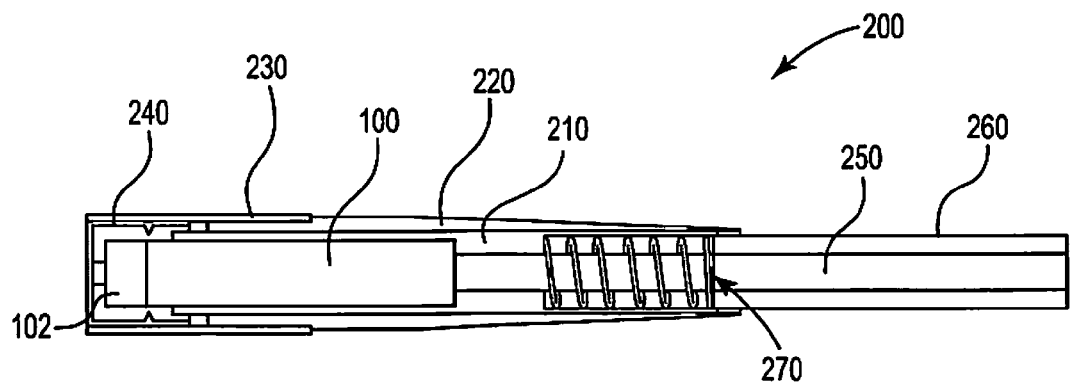

In FIGS. 7A and 7B the holder 200 is in an extinguishment position in which the second sleeve 230 is positioned over retainers 240 and thus over the heat source 102. The sleeve 230 restricts air flow to the heat source to extinguish the heat source 102.

Figure 8B:
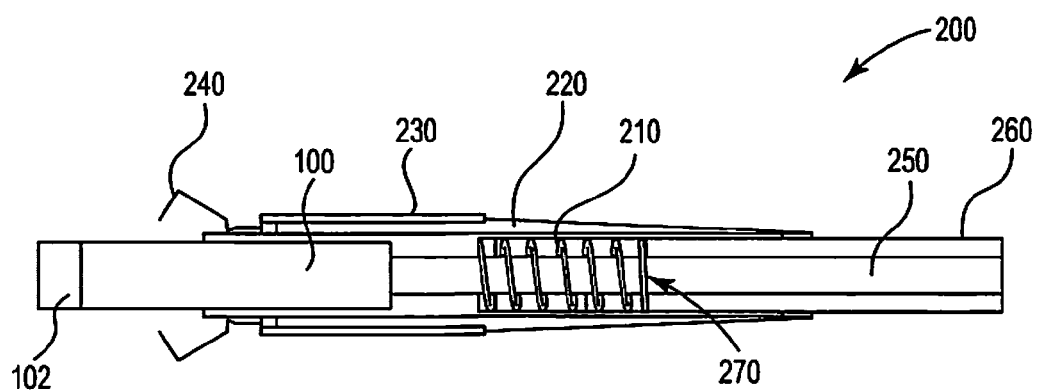

In FIGS. 8A and 8B the holder 200 is in an ejection position in which a mouth end of the mouthpiece 260 is distally collapsed, causing tube 240 to advance distally within the passage of the body 210 to eject the aerosol generating article 100 from the passage of the body 210. Sleeve 210 is retracted and thus retainers 240 are deflected to allow ejection of the aerosol generating article.

Thus, methods, systems, apparatuses, assemblies and articles for a holder for aerosol generating articles are described. Various modifications and variations of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are apparent to those skilled in the mechanical arts and aerosol generating article manufacturing or related fields are intended to be within the scope of the following claims.

The invention claimed is:

1. A holder for an aerosol generating article having a heat source, the holder comprising:
a body defining a passage configured to receive the aerosol generating article; and
a retainer longitudinally moveable relative to the body from a first position to a second position, the retainer comprising a deflectable arm and a retention member extending from the arm and configured to retain the aerosol generating article within the passage of the body when the retainer is in the first position, wherein movement of the retainer to the second position causes the arm to deflect to provide access for introducing or withdrawing the aerosol generating article from the passage of the body,
wherein the body and the retainer are configured such that, when the retainer is in the first position, the retention member extends distally beyond the heat source of the aerosol generating article when the aerosol generating article is received in the passage of the body and during use of the aerosol generating article,
wherein the body and the retainer are configured to receive an aerosol generating article having a length of 65 millimeters to 100 millimeters.

2. The holder according to claim 1, comprising a plurality of retainers longitudinally moveable relative to the body from a first position to a second position, wherein when retainers are in the first position the retainers are configured to surround the heat source of the aerosol generating article.

3. The holder according to claim 2, wherein the plurality of retainers, when in the first position and surrounding the heat source, are arranged and configured to allow air flow to the heat source for combustion of the heat source.

4. The holder according to claim 1, wherein the deflectable arm of the retainer comprises a bend portion.

5. The holder according to claim 4, wherein the bend portion extends beyond an end of the body when the retainer is in the first position, and wherein the bend portion contacts an exterior surface of the body when the retainer is in the second position.

6. The holder according to claim 1, further comprising a first sleeve movable over the body, wherein the retainer is coupled to the first sleeve and extends beyond an end of the first sleeve, wherein moving the sleeve about the body can cause the retainer to move between the first and second positions.

7. The holder according to claim 1, further comprising an extinguishment sleeve slidable relative to the body between an extended position and a retracted position, wherein in the extended position the extinguishment sleeve is configured to extend over at least a portion of the heat source of the aerosol generating article received in the passage of the body, wherein in the extended position the extinguishment sleeve is configured to limit air flow to the heat source, and wherein in the retracted position the extinguishment sleeve is configured to allow air to flow to the heat source.

8. The holder according to claim 7, wherein the extinguishment sleeve, in the extended position, extends over the retainer.

9. The holder according to claim 1, further comprising a tube sildably received in the passage of the body, wherein the tube is slidable within the passage of the body between a use position and an ejection position, and wherein sliding the tube in the passage of the body from the use position to the ejection position causes the aerosol generating article to be ejected from the passage of the body.

10. The holder according to claim 9, wherein the tube is biased towards the retention position.

11. The holder according to claim 9, wherein the tube defines a bore extending the length of the tube and is arranged and configured for aerosol from the aerosol generating article to flow through the bore.

12. An assembly comprising the holder according to claim 1 and the aerosol generating article having the heat source, wherein the aerosol generating article is received in the aperture defined by the body of the holder.

13. A kit comprising the holder according to claim 1 and one or more aerosol generating articles having a heat source, wherein the aerosol generating articles are configured to be received in the passage of the body of the holder.

14. The kit according to claim 13, wherein the aerosol generating article comprises an aerosol generating substrate and wherein the aerosol generating article is configured to transfer heat from the heat source to the aerosol generating substrate without combusting the aerosol generating substrate.

15. The kit according to claim 14, wherein the aerosol generating substrate comprises tobacco.

16. The assembly according to claim 12, wherein the aerosol generating article comprises an aerosol generating substrate and wherein the aerosol generating article is configured to transfer heat from the heat source to the aerosol generating substrate without combusting the aerosol generating substrate.

17. The assembly according to claim 16, wherein the aerosol generating substrate comprises tobacco.

18. The assembly according to claim 17, wherein the aerosol generating article is configured such that the heat source heats the aerosol generating substrate primarily by conduction.

19. The kit according to claim 15, wherein the aerosol generating article is configured such that the heat source heats the aerosol generating substrate primarily by conduction.

20. The holder according to claim 3, wherein the plurality of retainers, when in the first position are arranged and configured to surround the heat source to form a cage about the heat source.

* * * * *